(12) United States Patent
Reynolds et al.

(10) Patent No.: US 7,491,694 B2
(45) Date of Patent: Feb. 17, 2009

(54) DENTAL RESTORATIVE MATERIALS

(75) Inventors: Eric C. Reynolds, Balwyn (AU); Martin J. Tyas, Ivanhoe (AU)

(73) Assignee: The University of Melbourne, Victoria (AU)

( * ) Notice: Subject to any disclaimer, the term of this patent is extended or adjusted under 35 U.S.C. 154(b) by 0 days.

(21) Appl. No.: 10/478,094

(22) PCT Filed: May 21, 2002

(86) PCT No.: PCT/AU02/00632

§ 371 (c)(1), (2), (4) Date: May 18, 2004

(87) PCT Pub. No.: WO02/094204

PCT Pub. Date: Nov. 28, 2002

(65) Prior Publication Data

US 2005/0063922 A1  Mar. 24, 2005

(30) Foreign Application Priority Data

May 21, 2001 (AU) ........................... PR5177

(51) Int. Cl.
*A61K 38/16* (2006.01)
*A61L 24/00* (2006.01)
*C07K 14/00* (2006.01)

(52) U.S. Cl. ................... 514/7; 424/435; 530/352

(58) Field of Classification Search ............... None
See application file for complete search history.

(56) References Cited

U.S. PATENT DOCUMENTS

| 5,520,725 A | 5/1996 | Kato et al. |
| 5,981,475 A | 11/1999 | Reynolds |
| 6,652,875 B1 * | 11/2003 | Bannister .................. 424/440 |

FOREIGN PATENT DOCUMENTS

| DE | 195 26 224 A1 | 1/1996 |
| WO | WO 82/03008 | 9/1982 |
| WO | WO 87/07615 | 12/1987 |
| WO | WO 94/00146 | 1/1994 |
| WO | WO 96/29340 | 9/1996 |
| WO | WO 97/36943 | 10/1997 |
| WO | WO 00/06108 | 2/2000 |
| WO | WO 98/40406 A | 11/2001 |

OTHER PUBLICATIONS

Crisp, S., "Glass Ionomer Cement: Chemistry of Erosion", J. Dent. Res. 55: 1032-1041 (1976).*
E.C. Reynolds, "Remineralization of Enamel Subsurface Lesions by Casein Phosphopeptide-stabilized Calcium Phosphate Solutions", J. Dent. Res., 76(9): 1587-1595, Sep. 1997.
Hidaka, S., et al., "Method of the Study of the Formation and Transformation of Calcium Phosphate Precipitates: Effects of Several Chemical Agents and Chinese Folk Medicines,"Archives of Oral Biology, vol. 36, No. 1, pp. 49-54 (1991).
Reynolds, E. C., et al., "Dairy Products and Dental Health," Proceedings of the Nutrition Society of Australia, pp. 95-102 (1995).
Huq, et al., "A 'H-NMR Study of the Casein Phosphopeptide α casein (59-79)." Biochimica et Biophysica Acta, vol. 1247, pp. 201-208 (1995).
Reynolds, E. C., et al., "Anticariogenicity of Calcium Phosphate Complexes of Tryptic Casein Phosphopeptides in the Rat," Journal of Dental Research, vol. 74, No. 6, pp. 1272-1279 (1995).
Holt, C., et al., "Ability of a β-casein Phosphopepetide to Modulate the Precipitation of Calcium Phospate by Forming Amorphous Dicalcium Phosphate Nanoclusters," Biochemical Journal, vol. 314, No. 3, pp. 1035-1039 (1996).
Adamson, A. et al., "The Analysis of Multiple Phosphoseryl-containing Casein Peptides Using Capillary Zone Electrophoresis," Journal of Chromatography, vol. 646, pp. 391-396 (1993).
Adamson, N.J., et al., "Characterization of Casein Phosphopeptides Prepared using Alcalase: Determination of Enzyme Specificity," Enzyme and Microbial Technology, vol. 19, pp. 202-207 (1996).
Wilkiel, K., et al., "Hydroxyapatite Mineralization and Demineralizaton in the Presence of Synthetic Phosphorylated Pentapeptides," Archives of Oral Biology, vol. 39, No. 8, pp. 715-721 (1994).
Akinmade, J. et al., "Review Glass-Ionomer Cements as Adhesives, Part 1, Fundamental Aspects and Their Clinical Relevance," Journal of Materials Science: Materials in Medicine, vol. 4, pp. 95-101 (1993).

\* cited by examiner

*Primary Examiner*—Jon P Weber
(74) *Attorney, Agent, or Firm*—Stephen A. Bent; Foley & Lardner LLP

(57) ABSTRACT

The present invention relates to a composition for dental restoration including a dental restorative material and an effective amount of a casein phosphopeptide(CPP)-amorphous calcium phosphate (ACP) complex or casein phosphopeptide(CPP)-amorphous calcium fluoride phosphate (ACFP) complex.

28 Claims, 2 Drawing Sheets

DENTAL RESTORATIVE MATERIALS

Figure 1:
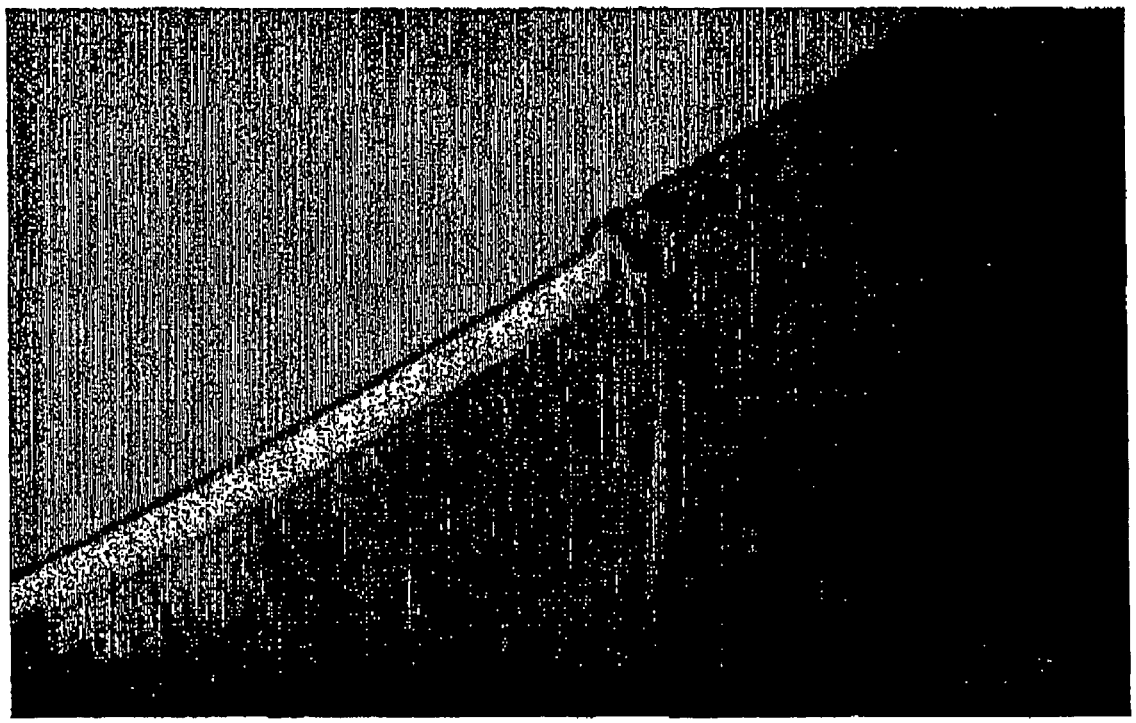

The present invention relates to dental restorative materials including amorphous calcium phosphates and/or amorphous calcium fluoride phosphates stabilised by phosphopeptides. These dental restorative materials have superior anticariogenic properties protecting tooth structures as they remineralise (repair) early stages of dental caries that may have developed around the restoration. Methods of making the dental restorative materials of the invention and of treatment or prevention of dental caries are also provided. The invention also provide a kit of parts including amorphous calcium phosphates and/or amorphous calcium fluoride phosphates stabilised by phosphopeptides.

BACKGROUND

Dental caries is initlated by the demineralisation of hard tissue of the teeth by organic acids produced from fermentation of dietary sugar by dental plaque odontopathogenic bacteria.

Dental caries is still a major public health problem and restored tooth surfaces can be susceptible to further dental caries around the margins of the restoration.

Casein phosphopeptide-amorphous calcium phosphate complexes (CPP-ACP) and CPP-stabillsed amorphous calcium fluoride phosphate complexes (CPP-ACFP) in solution have been shown to prevent enamel deminerallsation and promote remineralisation of enamel subsurface lesions in animal and human in situ caries models [Reynolds 1997 patent application, PCT/AU98/00160].

The active CPP have been specified in the U.S. Pat. No. 5,015,628 and include peptides Bos $\alpha_{s1}$-casein X-5P (f59-79) [1], Bos β-casein X-4P (f1-25) [2], Bos $\alpha_{s2}$-casein X-4P (f46-70) [3] and Bos $\alpha_{s2}$-casein X-4P (f1-21) [4] as follows:

[1] $Gln^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gin-$Lys^{79}$. $\alpha_{s1}$(59-79)

[2] $Arg^1$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-$Arg^{25}$. β(1-25)

[3] $Asn^{46}$-Ala-Asn-Glu-Glu-Glu-Tyr-Ser-Ile-Gly-Ser(P)-Ser(P)-Glu-Glu-Ser(P)-Ala-Glu-Val-Ala-Thr-Glu-Glu-Val-$Lys^{70}$. $\alpha_{s2}$(46-70)

[4] $Lys^1$-Asn-Thr-Met-Glu-His-Val-Ser(P)-Ser(P)-Ser(P)-Glu-Glu-Ser-Ile-Ile-Ser(P)-Gin-Glu-Thr-Tyr-$Lys^{21}$. $\alpha_{s2}$(1-21)

These peptides stabilise novel forms of very soluble amorphous calcium phosphate and amorphous calcium fluoride phosphate [Reynolds 1997 patent application, PCT/AU98/00160].

Glass ionomer cements (GICs) are water-based, tooth coloured and chemically adhesive materials used in dentistry as bases and restorations. Microleakage around restorations remains a significant problem, which can lead to caries of the underlying tooth tissues (Bergenholtz et al., 1982; Davis et al., 1993; Pachuta and Meiers, 1995). However, GICs are ion-releasing materials and the incorporation and slow release of fluoride ions from the cement provides a significant anticariogenic property (Forss, 1993; Williams et al., 1999)

Although H would be expected that inclusion of CPP-ACP into a GIC would result in the incorporation of the calcium ions into the GIC matrix making them unavailable, surprisingly, we have discovered that incorporation of CPP-ACP into a standard, commercially-available GIC resulted in a GIC with unexpected superior properties in terms of microtensile bond strength. Comprehensive strength and ion-release. In fact, surprisingly the GIC containing CPP-ACP was able to significantly remineralize the underfying dentine whereas the standard GIC could not. These results form the basis of this invention which is novel dental restorative materials containing CPP-ACP or CPP-ACFP with superior physicochemical and anticariogenic properties.

SUMMARY OF THE INVENTION

The present invention relates to a composition for dental restoration including a dental restorative material and an effective amount of a casein phosphopeptide(CPP)-amorphous calcium phosphate (ACP) complex or casein phosphopeptide(CPP)-amorphous calcium fluoride phosphate (ACFP) complex.

According to one aspect of the invention, there is provided a composition for dental restoration, including a dental restorative material to which has been added amorphous calcium phosphate (ACP) or amorphous calcium fluoride phosphate (ACFP) stabilized by phosphopeptides containing the amino acid sequence —Ser(P)-Ser(P)-Ser(P)—. Preferably, the ACP and ACFP are formed under alkaline conditions. The amorphous calcium phosphate is preferably of the approximate formula $Ca_3(PO_4)_2 \cdot xH_2O$ where $x \geq 1$, ie there are one or more $H_2O$ per $Ca_3(PO_4)_2$. The calcium phosphate derivative may be a calcium fluoride phosphate of approximate formula $Ca_2F(PO_4) \cdot xH_2O$ where $x \geq 1$ providing amorphous calcium fluoride phosphate (ACFP). More preferably the calcium phosphate derivative may be a mixture of ACP and ACFP in the ratio n:1, where n is an integer $\geq 1$, eg 1:1 giving $Ca_5F(PO_4)_3$ or 2:1 giving $Ca_8F(PO_4)_5$.

It is expected that the exact ratios described above, and the proportions of components in the amorphous calcium phosphate, will be different in the final composition due, for example, to interactions between components.

The phosphopeptide may be from any source; it may be obtained by tryptic digestion of casein or other phospho-acid rich proteins or by chemical or recombinant synthesis, provided that it comprises the core sequence -Ser(P)-Ser(P)-Ser(P)-. The sequence flanking this core sequence may be any sequence. However, those flanking sequences in $\alpha_{s1}$(59-79) [1], β(1-25) [2], $\alpha_{s2}$(46-70) [3] and $\alpha_{s2}$(1-21) [4] are preferred. The flanking sequences may optionally be modified by deletion, addition or conservative substitution of one or more residues. The amino acid composition and sequence of the flanking region are not critical as long as the conformation of the peptide is maintained and that all phosphoryl and caboxyl groups interacting with calcium ions are maintained as the preferred flanking regions appear to contribute to the structural action of the motif.

The base of the dental restorative material can be a glass ionomer cement, a composite material or any other restorative material which is compatible. It is preferred that the amount of CPP-ACP complex or CPP-ACFP complex included in the dental restorative material is 0.01-80% by weight, preferably 0.5-10% and more preferably 1-5% by weight. The dental restorative material of this invention which contains the above mentioned agents may be prepared and used in various forms applicable to dental practice. The dental restorative material according to this invention may further include other ions, eg. antibacterial ions $Zn^{2+}$, $Ag^+$, etc or other additional ingredients depending on the type and form of a particular dental restorative material. It is preferable that the pH of the CPP-ACP complex or CPP-ACFP complex be between 2-10, more preferably 5-9 and even more preferably 7-9. It is preferable that the pH of the dental restorative material containing the CPP-ACP complex or ACFP complex be between 2-10, more preferably 5-9 and even more preferably 7-9.

The invention is also directed to a method of manufacture of a restorative composition. Preferably, the method includes the addition of ACP and/or ACFP, stabilised by phosphopeptides as stated above, to a base dental restorative material.

The invention also relates to use of a restorative composition as stated above for the treatment and/or prevention of dental caries.

The invention also provides a method of treatment and/or prevention of dental caries in animals including providing the composition according to the invention or manufactured according to the invention and applying to teeth in an animal in need of treatment and/or prevention.

The invention also relates to a kit of parts including (a) dental restorative material and (b) CPP-ACP complex or CPP-ACFP complex together with instructions for their use for the preparation of a composition for dental restoration.

The invention also relates to a kit of parts including (a) dental restorative material (b) casein phosphopeptide (c) calcium ions and (d) phosphate ions, and optionally flouride ions, together with instructions for their use for the preparation of a composition for dental restoration.

It will be clearly understood that, although this specification refers specifically to applications in humans, the invention is also useful for veterinary purposes. Thus in all aspects the invention is useful for domestic animals such as cattle, sheep, horses and poultry, for companion animals such as cats and dogs; and for zoo animals.

FIGURES

FIG. 1: Longitudinal section of root of tooth restored with GIC treated with acid buffer solution and visualised using polarized-light microscopy.

Figure 2:
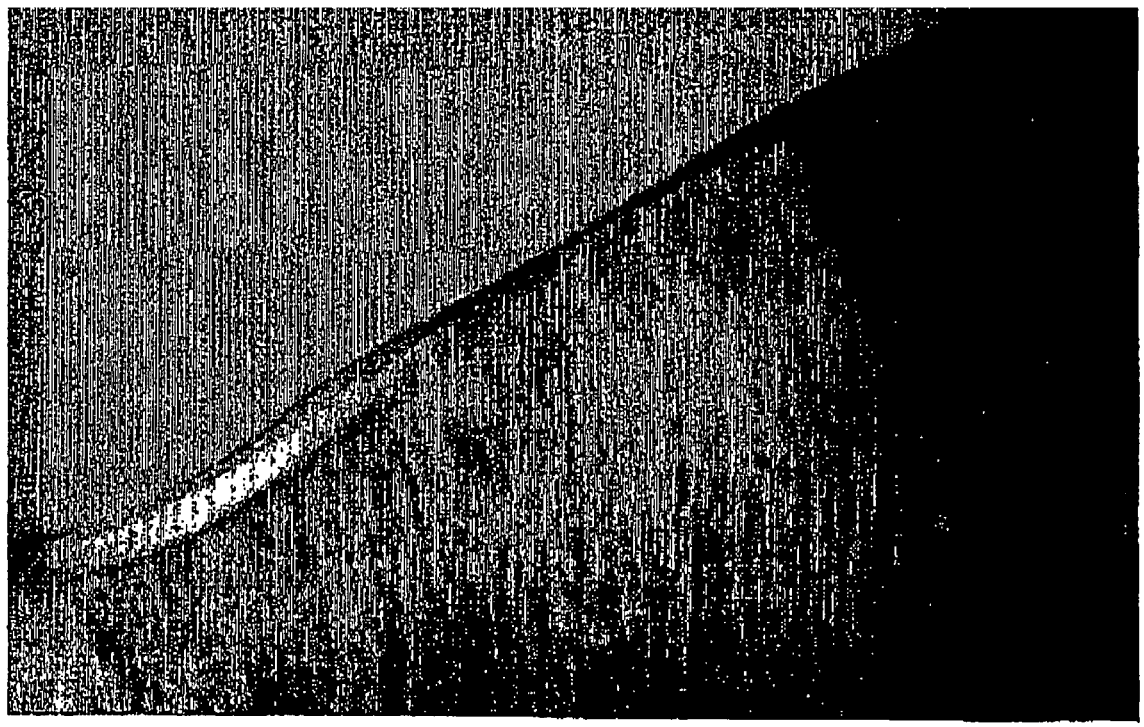

FIG. 2: Longitudinal section of root of tooth restored with GIC containing CPP-ACFP, treated with acid buffer solution and visualised using polarized-light microscopy.

DETAILED DESCRIPTION OF THE INVENTION

The invention will now be described in detail by way of reference only to the following non-limiting Examples.

EXAMPLE 1

Incorporation of CPP-ACP Into a Glass Ionomer Cement

Preparation of GIC Containing CPP-ACP for Compressive Strength and Wet Setting Time Assays Twenty-four cylinders, 4 mm diam×6 mm long, were made from a glass ionomer cement (GICs) for the compressive strength test and twelve discs, 10 mm diam×5 mm thick, for the net setting time test. Four groups (A, B, C, D) were formed with the specimens (Table 1). Six specimens per group were made for the compressive strength test and three specimens per group for the net setting time test.

Group A (control) was prepared using a self-curing glass ionomer cement (Fuji IX GP, liquid batch No. 080561 and powder batch No. 061051, GC International, Tokyo, Japan). Groups B, C and D were prepared from the same GIC, containing 0.78, 1.56 and 3.91% w/w CPP-ACP respectively incorporated at a powder:liquid ratio of 3.6:1. The CPP-ACP (Recaldent™) was obtained from Bonlac foods Ltd (Melbourne, Australia). For the experimental groups, the CPP-ACP and the GIC powders were manually mixed and shaken in a plastic container, and kept at 4° C. until the preparation of the specimens. The GIC liquid and the powder:liquid ratio used for all the specimens were as indicated by the commercial manufacturer of the GIC. The product was allowed to reach room temperature before mixing. For all the groups, the powder and the liquid were manually mixed for 20 s and the mixture was then placed into the molds for each corresponding test Compressive strength and net setting time tests were performed following ISO methods (ISO, 1991).

Microtensile Bond Strength to Dentin

Non-carious human molars stored in saline solution containing thymol were used within two months following extraction. Seventeen bar-shaped specimens, half GIC and half dentin, were prepared using GIC (Fuji IX GP, batch No.9909021, GC International, Japan) containing 1.56% w/w CPP-ACP as described above. Control specimens (n=17) were prepared using the normal GIC. The liquid and the power:liquid ratio for all the specimens remained the same as for the commercial product. Microtensile bond strength tests were performed following a previously described method (Phrukkanon et al., 1998; Tanumiharja et al., 2000), stressing the specimens in tension at a cross-head speed of 1 mm/min until failure. Mean bond strength values were calculated using the standard formula (ISO, 1991), and the fractured specimens observed in a scanning electron microscope (SEM 515; Phillips, Eindhoven, The Netherlands) to assess the mode of failure.

Ion Measurements and CPP Detection

Twelve discs, 6 mm diam×2 mm thick, were prepared using the experimental GIC formula containing 1.56% w/w CPP-ACP and twelve controls were prepared from the unmodified GIC. The GIC was mixed, as described above, injected into the molds, condensed and allowed to set at 37° C. and 100% RH for 1 h. During setting, the bottom and top of the filled molds were covered by mylar strips and microscope slides under hand pressure. The discs were removed from the molds and placed into individual sealed plastic tubes. Six of the experimental discs were incubated at 37° C. in 2 mL deionized water pH 6.9 (Milli-Q Reagent water System, Millipore Corporation), and the other six in 50 mM sodium lactate (Ajax Chemicals, Auburn, NSW) buffer at pH 5.0. The same procedure was followed with the controls. The solutions were changed every 24 h for 3 days and the release of calcium, inorganic phosphate and fluoride ions was measured in each solution. Calcium concentrations were determined using atomic absorption spectrophotometry (Adamson and Reynolds 1995), inorganic phosphate colorimetrically (Itaya and UI, 1966) and fluoride ion using an ion selective electrode (Ion 85 Radiometer, Copenhagen, Denmark). The release of the ions was expressed as μmol/mm$^2$ surface area of the GIC exposed.

The presence of CPP in the solutions was determined using Matrix Assisted Laser Desorption/Ionisation—Mass Spectrometry (MALDI-MS) (Voyager-DE, Perseptive Blosystems; Farmingham, Mass., USA) with a matrix of 2,5-dehydroxy benzoic acid in 66% water, 33% $CH_3CN$ and 1% formic acid.

Statistical Analysis

Data from compressive strength and net setting time tests were subjected to one-way analysis of variance (ANOVA), using least-significant differences (LSD) for the compressive strength and Bonferroni test for the not setting time. Data from the microtensile bond strength were compared using Student's t test ($p<0.05$). Chi squared distribution ($p<0.05$)

was used to detect the mode of failure of fractured specimens. Data from the ion release analyses were compared using Student's t test (p<0.05).

RESULTS

Compressive Strength and Net Setting Time

Mean values for the compressive strength and net setting times for the GICs are shown in Table 1. The mean compressive strengths for all specimens ranged from 118.3 MPa to 169.6 MPa, with the highest value being obtained for the GIC containing 1.56% CPP-ACP. The mean net setting times ranged from 523s to 186 s, but only specimens containing 3.91% CPP-ACP (Group D) were significantly different from the others.

Microtensile Bond Strength to Dentin

Table 2 shows the mean microtensile bond strength values for the GIC containing 1.56% w/w CPP-ACP and control and the mode of failure for the fractured specimens. A significantly higher bond strength value was found in the CPP-ACP-containing GIC (10.59±4.00 MPa) than in the control (7.97±2.61 MPa). The distribution in the mode of failure as analysed using SEM was also found to be significantly different (p<0.05). Type 2 fracture was more frequent with the CPP-ACP-containing GIC, whereas Type 4 was more frequent with the control (Table 2). The microstructure of the two cements examined by SEM at a 360× magnification seemed generally similar, although there appeared to be a more porous and roughened fracture surface with the controls relative to the CPP-ACP-containing cements.

Ion and CPP Release

Mean values for the release of fluoride, calcium and phosphate in water (pH 6.9) and sodium lactate buffer (pH 5.0) from the GIC containing 1.56% w/w CPP-ACP and the control GIC are shown in Tables 3, 4 and 5. The pattern of fluoride release in water was similar between samples and controls, with the highest release occurring during the first 24 h and a slower but continued release during the next two 24-h periods (Table 3). Fluoride release was significantly higher in the pH 5.0 sodium lactate buffer than in pH 6.9 water for both materials, the CPP-ACP-containing GIC and the control GIC. Significantly higher fluoride release was found with the CPP-ACP-containing GIC than with the control at both pH values (Table 3).

Calcium release values from the GICs are shown in Table 4. No calcium was released at neutral pH in water either from the CPP-ACP-containing GIC or from the control. Calcium release was found only in the CPP-ACP-containing GIC in the pH 5.0 sodium lactate buffer. The release was low relative to the fluoride but continuous during the three 24 h periods (Table 4).

Inorganic phosphate release from the GICs in water (pH 6.9) and sodium lactate buffer (pH 5.0) is shown in Table 5. At both pH values phosphate release was significantly higher from the CPP-ACP-containing GIC than from the controls during the first 24-h period. The release of inorganic phosphate was significantly higher in sodium lactate buffer at pH 5.0 than in water at pH 6.9 for both materials.

MALDI-MS analysis of the sodium lactate buffer (pH 5.0) and the water (pH 6.9) after 24 h incubation with the GIC containing 1.56% w/w CPP-ACP and control GIC revealed that the CPP could be detected in the pH 5.0 buffer after incubation with the CPP-ACP containing GIC only. The mass spectrum obtained was the same as that observed with standard CPP-ACP.

Conclusion

Stabilized complexes of CPP-ACP were incorporated into the glass powder of a GIC and, in contrast to what would have been expected, at least some of the calcium ions, phosphate ions and CPP were not bound into the GIC matrix but were released to produce a cement with superior physicochemical and anticariogenic properties.

A major reason for using GICs in a variety of clinical applications is their capacity to chemically bond to different surfaces such as enamel, dentin and resin composite (Akinmade and Nicholson, 1993). GICs are used routinely in conjunction with resin composites (LI et al., 1996; Pereira et al., 1998), in Atraumatic Restorative Treatment (ART) (Frencken et al., 1996), in tunnel restorations (Svanberg, 1992) and in restoration of primary teeth (Frankenberger et al., 1997). Bond strength, therefore, is an important property of the GIC. The mean microtensile bond strength value of the CPP-ACP-containing GIC was superior to that of the control GIC. The testing method used has been successfully used on specimens with different dentin thickness, dentinal tubule orientation and with disease-affected dentin specimens (Phrukkanon et al., 1998). Therefore, factors such as the quality, depth and moisture of the dentin substrate (Burrow et al., 1994; Tagami et al., 1993) did not affect the results of this study.

The most common mode of failure in the adhesion between a GIC and the dentin during microtensile bond strength tests is Type 4, i.e., cohesive failure within the GIC (Tanumlharja et al., 2000). This was the predominant mode of failure of the control GIC found in this study. The predominant mode of fracture for the CPP-ACP-containing GICs, was Type 2, i.e. partial cohesive failure in the GIC and partial adhesive failure between the GIC and the dentine.

With respect to the release of ions from the CPP-ACP-containing GIC and controls, it was shown that the fluoride release in sodium lactate buffer pH 5.0 was significantly higher than in water (pH 6.9). This finding has been previously reported for normal GICs (Forss, 1993; Kuhn and Wilson, 1985). However, in this study fluoride release was significantly higher from the CPP-ACP-containing GIC than the GIC-controls at both pH values which was an unexpected result. Without being bound by any theory, it would appear that the CPP-ACP promotes the release of fluoride ions from the GIC, probably by forming casein phosphopeptide-amorphous calcium fluoride phosphate (CPP-ACFP) complexes, which are released from the cement matrix.

Significantly more inorganic phosphate was released from the CPP-ACP GIC at both pH values (5.0 and 6.9) than that released from the control GIC.

In this example, total rates of release from the CPP-ACP-containing GIC after 72 h at Ph 5.0 were 72.25±9.99 µmol/mm$^2$ for fluoride, 1.85±0.1 µmol/mm$^2$ for inorganic phosphate and 0.92±0.15 µmol/mm$^2$ for calcium ions. The higher microtensile bond strength of the CPP-ACP-containing GIC and the capacity of the cement to release CPP-ACFP complexes indicates that the 1.56%-CPP-ACP-containing GIC was a superior restorative/base with an improved anticariogenic potential.

EXAMPLE 2

Remineralisation of Dentine by Release of CPP-ACFP from a GIC Containing CPP-ACFP Freshly extracted and caries-free human third molars, with no cracks and defects, stored in normal saline solution were used to prepare two box-shaped cavities, 7 mm long×3 mm wide×1.5 mm deep, along the cemento-enamel junction of both mesial and distal surfaces, using a cylindrical diamond bur, high-speed turbine and air-water coolant. The cavity margins were finished with a slow-speed cylindrical diamond bur to achieve a cavo-surface angle as close as possible to 90°. The teeth were divided into two groups (A, B). Teeth from group A were restored with a self-curing GIC (Fuji IX GP capsulated, batch No. 140493, GC International, Tokyo, Japan), and teeth from group B, the experimental group, was restored using the same GIC plus 1.56% w/w CPP-ACP prepared as in Example 1. The GIC liquid and the powder:liquid ratio for all the specimens remained as for the commercial product. The materials were mixed at room temperature, placed into the cavities using a plastic spatula and allowed to set at 37° C. and 100% RH for 1 h. The restorations were finished and polished with fine polishing discs (Soflex, 3M) under running water to ensure all margins are exposed, and the integrity of each cavo-surface margin was confirmed under a light microscope at 20× magnification.

The roots of the teeth containing the GIC restoration were cut using a slow-speed diamond saw under copious water spray. Two coats of nail varnish were applied to the entire tooth surface, leaving only a 1-mm window around the cavity margins. Each tooth was stored in an individual plastic vial containing 25 ML of acid buffer solution consisting of 2.2 mM calcium chloride, 2.2 mM sodium dihydrogen orthophosphate and 50 mM acetic acid at pH 5.0. The teeth were stored in the solution for four days, and the solution was refreshed every 24 h.

The specimens were removed from the demineralising solution, rinsed under tap water thoroughly and cut through the restorations with a water-cooled diamond saw microtome, to produce longitudinal sections which were ground to 100 μm thickness. The resulting slides were evaluated for lesion formation using polarized-light microscopy with quinoline as imhibition medium (FIG. 1 and FIG. 2).

FIG. 1 shows a substantial subsurface lesion in the dentine adjacent to the GIC restoration with very little protection being provided by the fluoride-releasing GIC. FIG. 2 on the other hand shows a poorly formed subsurface lesion with dramatic protection (remineralisation) provided by the release of CPP-ACFP from the GIC. These results show that the inclusion of CPP-ACP into a fluoride-releasing GIC produces a remarkable ability to remineralize (repair) early stages of decay around GIC restorations.

Other advantages and modifications to the basic invention and its construction as described above will be apparent to those skilled in the art and all modifications and adaptations are included in the scope of the invention.

TABLES

TABLE 1

Compressive strength (MPa) and net setting time (s) for CPP-ACP-containing GIC and controls

| Group | CPP-ACP (% w/w) | Compressive strength | Net setting time |
|---|---|---|---|
| A | 0.00 | 137.8 ± 40.7[a] | 186 ± 5[b] |
| B | 0.78 | 153.7 ± 24.7 | 210 ± 17 |
| C | 1.56 | 169.6 ± 28.6 | 226 ± 35 |
| D | 3.91 | 118.6 ± 12.5 | 523 ± 35[c] |

[a]Mean ± standard deviation, n = 6. No significant differences in compressive strength between groups (A, B, C, D).
[b]Mean ± standard deviation; n = 3.
[c]Significantly different from the other setting times ($p < 0.05$).

TABLE 2

Microtensile bond strength (MPa) and mode of failure on 1.56% w/w CPP-ACP-containing GIC and control

| Group | Bond Strength | Type 1[b] | Type 2 | Type 3 | Type 4 | Total |
|---|---|---|---|---|---|---|
| 1.56% w/w CPP-ACP/ GIC | 10.59 ± 4.00[a] | 2[c] | 11[d] | 0 | 4 | 17 |
| Control GIC | 7.97 ± 2.61 | 2 | 5 | 0 | 10 | 17 |

[a]Mean and standard deviation; significantly different from control group ($p < 0.05$)
[b]Mode of failure:
Type 1 adhesive failure between the restoration and the dentin;
Type 2 partial adhesive failure between the GIC and the dentin and partial cohesive failure in the GIC;
Type 3 cohesive failure in the dentin;
Type 4 cohesive failure in the GIC
[c]Mean frequency value
[d]Significantly different from control group ($p < 0.05$)

TABLE 3

Fluoride release from CPP-ACP-containing GIC and control at neutral and acid pH

| | Fluoride release (μmol/mm$^2$) | | | |
|---|---|---|---|---|
| | Water (pH 6.9) | | Sodium Lactate (pH 5.0) | |
| Period | CPP-ACP GIC | Control GIC | CPP-ACP GIC | Control GIC |
| 1$^{st}$ 24 h | 16.70 ± 2.43[a,b,c] | 10.07 ± 1.20[d] | 34.52 ± 8.16[c] | 24.80 ± 0.47[d] |
| 2$^{nd}$ 24 h | 5.19 ± 0.79[b,c] | 3.17 ± 0.30[d] | 19.12 ± 4.26[c] | 14.50 ± 1.41[d] |
| 3$^{rd}$ 24 h | 3.35 ± 0.07[b,c] | 2.42 ± 0.14[d] | 18.61 ± 3.29[c] | 15.33 ± 0.89[d] |
| Total | 24.67 ± 3.99[b,c] | 15.66 ± 1.58[d] | 72.25 ± 9.99[c] | 54.64 ± 1.38[d] |

[a]Mean ± standard deviation, n = 6.
[b]Significantly different ($p < 0.05$) from control value at the same pH.
[c]Significantly different ($p < 0.05$) from CPP-ACP GIC value at different pH.
[d]Significantly different ($p < 0.05$) from control value at different pH.

TABLE 4

Calcium release from CPP-ACP-containing GIC and control at neutral and acidic pH

| | Calcium release (μmol/mm$^2$) | | | |
|---|---|---|---|---|
| | Water (pH 6.9) | | Sodium Lactate (pH 5.0) | |
| Period | CPP-ACP GIC | Control GIC | CPP-ACP GIC | Control GIC |
| 1$^{st}$ 24 h | —[a] | — | 0.35 ± 0.07[b,c,d] | — |
| 2$^{nd}$ 24 h | — | — | 0.31 ± 0.07[c,d] | — |
| 3$^{rd}$ 24 h | — | — | 0.26 ± 0.05[c,d] | — |
| Total | — | — | 0.92 ± 0.15[c,d] | — |

[a]No calcium ion release detected.
[b]Mean ± standard deviation, n = 6
[c]Significantly different ($p < 0.05$) from control value at the same pH.
[d]Significantly different ($p < 0.05$) from sample value at different pH.

TABLE 5

Phosphate release from CPP-ACP-containing GIC and control at neutral and acidic pH

| | Inorganic phosphate release (μmol/mm$^2$) | | | |
|---|---|---|---|---|
| | Water (pH 6.9) | | Sodium Lactate (pH 5.0) | |
| Period | CPP-ACP GIC | Control GIC | CPP-ACP GIC | Control GIC |
| 1$^{st}$ 24 h | 0.36 ± 0.07$^{a,b,c}$ | 0.02 ± 0.00$^d$ | 0.88 ± 0.15$^{b,c}$ | 0.53 ± 0.05$^d$ |
| 2$^{nd}$ 24 h | 0.09 ± 0.13$^c$ | 0.01 ± 0.01$^d$ | 0.48 ± 0.03$^c$ | 0.53 ± 0.03$^d$ |
| 3$^{rd}$ 24 h | 0.02 ± 0.01$^c$ | 0.01 ± 0.01$^d$ | 0.48 ± 0.05$^c$ | 0.49 ± 0.03$^d$ |
| Total | 0.49 ± 0.10$^{b,c}$ | 0.15 ± 0.10$^d$ | 1.85 ± 0.13$^{b,c}$ | 1.55 ± 0.06$^d$ |

$^a$Mean ± standard deviation, n = 6.
$^b$Significantly different (p < 0.05) from control value at the same pH.
$^c$Significantly different (p < 0.05) from CPP-ACP GIC value at different pH.
$^d$Significantly different (p < 0.05) from control value at different pH.

REFERENCES

Adamson N J, Reynolds E C (1995), Characterisation of tryptic casein phosphopeptides prepared under industrially-relevant conditions. *Biotech. Bioeng.* 45:96-204

Akinmade A O, Nicholson J W (1993). Glass-ionomer cements as adhesives. Part I fundamental aspects and their clinical relevance. *J Mater Scien: Mater In Medicin* 4:93-101.

Bergenholtz G, Cox C, Loesche W, Syed S (1982). Bacterial leakage around dental restorations: its effect on the dental pulp. *J Oral Pathol* 11:439-450.

Burrow M F, Takakura H, Nakajima M, Inai N, Tagami J, Takatsu T (1994). The influence of age and depth of dentin on bonding. *Dent Mater* 10:241-246.

Davis E L, Yu X, Joynt R B, Wieczkowski G, Glordano L (1993). Shear strength and microleakage of light-cured glass ionomers. *Am J Dent* 6:127-129.

Forss H (1993). Release of fluoride and other elements from light-cured glass ionomers in neutral and acidic conditions. *J Dent Res* 72:1257-1262.

Frankenberger R, Sindel J, Kramer N (1997). Viscous glass-ionomer cements: a new alternative to amalgam in the primary dentition? *Quintessence Int* 28:667-676.

Frencken J, Songpaisan Y, Phantumavanit P, Pilot T (1996). Atraumatic restorative treatment (ART): rationale, technique and development. *J Public Dent Health Dent* 56:135-140.

ISO (1991). International Organization for Standarization. ISO 9917-Dental water-based cements. Geneva.

Itaya K, UI M (1966). A new micromethod for the colorimetric determination of inorganic phosphate. *Clin Chim Acta* 14:361-366.

Kuhn A, Wilson A (1985). The dissolution mechanisms of silicate and glass-ionomer dental cements. *Biomat* 6:378-382.

Li J, Liu Y, Soremark R, Sundstrom F (1996). Flexure strength of resin-modified glass ionomer cements and their bond strength to dental composites. *Acta Odontol Scand* 54:55-58.

Pachuta S M, Meiers J C (1995). Dentin surface treatment and glass ionomer microleakage, *Am J Dent* 8:187-190.

Pereira P N, Yamada T, Inohoshi S, Burrow M F (1998). Adhesion of resin-modified glass ionomer cements using resin bonding systems. *J Dent* 26:479-485.

Phrukkanon S, Burrow M, Tyas M (1998). Effect of cross-sectional surface area on bond strengths between resin and dentin. *Dent Mater* 14:120-128.

Reynolds E (1997). Remineralization of enamel subsurface lesions by casein phosphopeptide-stabilized calcium phosphate solutions. *J Dent Res* 76:1587-1595.

Svanberg M (1992). Class II amalgam restorations, glass ionomer tunnel restorations, and caries development on adjacent tooth surfaces: a 3-year clinical study. *Caries Res* 26:315-318.

Tagami J. Nakajima M. Shono T. Takatsu T. Hosoda H (1993). Effect of aging on dentin bonding. *Am J Dent* 6:145-147.

Tanumiharja M, Burrow M, Tyas M (2000). Microtensile bond strengths of glass ionomer (polyalkenoate) cements to dentine using four conditioners. *J Dent* 28:361-366.

Williams J, Billington R, Pearson G (1999). Comparison of ion release from a glass ionomer cement as a function of the method of incorporation of added ions. *Biomat* 20:589-594.

Wilson A, McLean J (1988). Glass-ionomer cement. Chicago, Ill.: Quintessence Publishing Co., Inc.

The invention claimed is:

1. A composition for dental restoration, comprising a glass ionomer dental cement and an effective amount of a casein phosphopeptide(CPP)-amorphous calcium phosphate (ACP) complex and/or casein phosphopeptide(CPP)-amorphous calcium fluoride phosphate (ACFP) complex.

2. A composition according to claim 1, wherein the CPP comprises the amino acid sequence -Ser(P)-Ser(P)-Ser(P)-.

3. A composition according to claim 1, wherein the ACP is formed under alkaline conditions.

4. A composition according to claim 1, wherein the ACFP is formed under alkaline conditions.

5. A composition according to claim 4, wherein the ACFP also contains ACP, wherein ACP and ACFP are in the ratio of n:1, where n is an integer $\geq 1$.

6. A composition according to claim 1, wherein the effective amount of the CPP-ACP complex or CPP-ACFP complex is 0.01 to 80% by weight.

7. A composition according to claim 1, having a pH from 2 to 10.

8. A composition according to claim 7, wherein the pH is from 5 to 9.

9. A composition according to claim 8, wherein the pH is from 7 to 9.

10. A kit of parts including (a) a glass ionomer dental cement and (b) CPP-ACP complex and/or CPP-ACFP complex, together with instructions for their use for the preparation of a composition according to claim 1.

11. A kit of parts including (a) a glass ionomer dental cement, (b) casein phosphopeptides, (c) calcium ions, and (d) phosphate ions, together with instructions for their use for the preparation of a composition according to claim 1.

12. A kit of parts according to claim 11, further including fluoride ions.

13. A composition according to claim 2, wherein the ACP is formed under alkaline conditions.

14. A composition according to claim 2, wherein the effective amount of the CPP-ACP complex or CPP-ACFP complex is 0.5 to 10% by weight.

15. A composition according to claim 3, wherein the effective amount of the CPP-ACP complex or CPP-ACFP complex is 0.5 to 10% by weight.

16. A composition according to claim 4, wherein the effective amount of the CPP-ACP complex or CPP-ACFP complex is 0.5 to 10% by weight.

17. A composition according to claim 5, wherein the effective amount of the CPP-ACP complex or CPP-ACFP complex is 0.5 to 10% by weight.

18. A composition according to claim 1, wherein the effective amount of the CPP-ACP complex or CPP-ACFP complex is 0.5 to 10% by weight.

19. A composition according to claim 18, wherein the effective amount is 1 to 5% by weight.

20. A kit of parts including (a) a glass ionomer dental cement and (b) CPP-ACP complex and/or CPP-ACFP complex, together with instructions for their use for the preparation of a composition according to claim 2.

21. A kit of parts including (a) a glass ionomer dental cement, (b) casein phosphopeptides, (c) calcium ions, and (d) phosphate ions, together with instructions for their use for the preparation of a composition according to claim 2.

22. A composition according to claim 1, wherein the phosphopeptide is obtained by tryptic digest of casein.

23. A composition according to claim 1, wherein the phosphopeptide is obtained by chemical or recombinant synthesis.

24. A composition for dental restoration, comprising a glass ionomer dental cement and 1.0 to 5.0% by weight of a releasable casein phosphopeptide (CPP)-amorphous calcium phosphate (ACP) complex and/or casein phosphopeptide (CPP)-amorphous calcium fluoride phosphate.

25. A composition according to claim 1, wherein the microtensile bond strength and/or compressive strength of the dental restorative is greater than the dental cement in the absence of the CPP-ACP complex and/or CPP-ACFP complex.

26. A composition according to claim 25, wherein the CPP comprises the amino acid sequence -Ser(P)-Ser(P)-Ser(P)-.

27. The composition according to claim 25, wherein the ACP is formed under alkaline conditions.

28. The composition according to claim 25, wherein the ACFP is formed under alkaline conditions.

* * * * *

SEQUENCE LISTING

```
<160> NUMBER OF SEQ ID NOS: 4

<210> SEQ ID NO 1
<211> LENGTH: 21
<212> TYPE: PRT
<213> ORGANISM: Bos sp.
<220> FEATURE:
<221> NAME/KEY: MISC_FEATURE
<222> LOCATION: (6)..(6)
<223> OTHER INFORMATION: Xaa is a phosphorylated Serine
<220> FEATURE:
<221> NAME/KEY: MISC_FEATURE
<222> LOCATION: (8)..(10)
<223> OTHER INFORMATION: Xaa is a phosphorylated Serine
<220> FEATURE:
<221> NAME/KEY: MISC_FEATURE
<222> LOCATION: (17)..(17)
<223> OTHER INFORMATION: Xaa is a phosphorylated Serine

<400> SEQUENCE: 1
```

```
Gln Met Glu Ala Glu Xaa Ile Xaa Xaa Xaa Glu Glu Ile Val Pro Asn
1               5                   10                  15

Xaa Val Glu Gln Lys
            20

<210> SEQ ID NO 2
<211> LENGTH: 25
<212> TYPE: PRT
<213> ORGANISM: Bos sp.
<220> FEATURE:
<221> NAME/KEY: MISC_FEATURE
<222> LOCATION: (15)..(15)
<223> OTHER INFORMATION: Xaa is a phosphorylated Serine
<220> FEATURE:
<221> NAME/KEY: MISC_FEATURE
<222> LOCATION: (17)..(19)
<223> OTHER INFORMATION: Xaa is a phosphorylated Serine

<400> SEQUENCE: 2

Arg Glu Leu Glu Glu Leu Asn Val Pro Gly Glu Ile Val Glu Xaa Leu
1               5                   10                  15

Xaa Xaa Xaa Glu Glu Ser Ile Thr Arg
            20                  25

<210> SEQ ID NO 3
<211> LENGTH: 25
<212> TYPE: PRT
<213> ORGANISM: Bos sp.
<220> FEATURE:
<221> NAME/KEY: MISC_FEATURE
<222> LOCATION: (11)..(13)
<223> OTHER INFORMATION: Xaa is a phosphorylated Serine
<220> FEATURE:
<221> NAME/KEY: MISC_FEATURE
<222> LOCATION: (16)..(16)
<223> OTHER INFORMATION: Xaa is a phosphorylated Serine

<400> SEQUENCE: 3

Asn Ala Asn Glu Glu Glu Tyr Ser Ile Gly Xaa Xaa Xaa Glu Glu Xaa
1               5                   10                  15

Ala Glu Val Ala Thr Glu Glu Val Lys
            20                  25

<210> SEQ ID NO 4
<211> LENGTH: 21
<212> TYPE: PRT
<213> ORGANISM: Bos sp.
<220> FEATURE:
<221> NAME/KEY: MISC_FEATURE
<222> LOCATION: (8)..(10)
<223> OTHER INFORMATION: Xaa is a phosphorylated Serine
<220> FEATURE:
<221> NAME/KEY: MISC_FEATURE
<222> LOCATION: (16)..(16)
<223> OTHER INFORMATION: Xaa is a phosphorylated Serine

<400> SEQUENCE: 4

Lys Asn Thr Met Glu His Val Xaa Xaa Xaa Glu Glu Ser Ile Ile Xaa
1               5                   10                  15

Gln Glu Thr Tyr Lys
            20
```